United States Patent [19]

Preti et al.

[11] 4,010,738

[45] Mar. 8, 1977

[54] METHOD OF PREDICTING AND DETECTING OVULATION

[75] Inventors: George Preti, Philadelphia; George Richardson Huggins, Wallingford, both of Pa.

[73] Assignee: The Trustees of the University of Pennsylvania, Philadelphia, Pa.

[22] Filed: Apr. 2, 1975

[21] Appl. No.: 564,348

Related U.S. Application Data

[63] Continuation-in-part of Ser. No. 519,220, Oct. 30, 1974.

[52] U.S. Cl. .............................. 128/2 R; 23/230 B; 23/253 TP; 128/2 W
[51] Int. Cl.² ........................................ A61B 10/00
[58] Field of Search ......................... 128/2 W, 2 R; 23/253 TP, 230 B

[56] References Cited

UNITED STATES PATENTS

| | | | |
|---|---|---|---|
| 3,037,496 | 6/1962 | Melges | 128/2 W |
| 3,406,015 | 10/1968 | Foster | 128/2 W UX |
| 3,406,016 | 10/1968 | Foster et al. | 128/2 W UX |
| 3,472,738 | 10/1969 | Foster | 128/2 W UX |
| 3,842,166 | 10/1974 | Bucalo | 128/2 W X |

OTHER PUBLICATIONS

Michael, R. P. et al., Science, May 28, 1971, vol. 172, pp. 964–966.
J.A.M.A., vol. 186, No. 5, Nov. 1963, pp. 19 & 20.
Marshall, J. R., Proceedings of a Research Conf., on Nat. Family Planning, Jan. 23–26, 1972, pp. 135–143.

Primary Examiner—Kyle L. Howell
Attorney, Agent, or Firm—Paul & Paul

[57] ABSTRACT

A method of monitoring the concentration of a given volatile organic compound, or of urea, or both, which compound(s) is commonly found in vaginal secretions is described as providing a reliable diagnostic indication of ovulation, and more particularly is described as providing a simple home-test method of predicting the onset of the fertile period, thereby increasing the reliability of the "rhythm method" of birth control.

20 Claims, 7 Drawing Figures

METHOD OF PREDICTING AND DETECTING OVULATION

RELATED APPLICATIONS

This is a continuation-in-part of our co-pending U.S. patent application Ser. No. 519,220, filed Oct. 30, 1974.

FIELD OF THE INVENTION

The present invention relates to the field of prediction, detection, and diagnosis of ovulation in female mammals through the detection of secondary characteristics occurring before, after or during ovulation, and more particularly to the prediction and detection of ovulation of these secondary characteristics as they appear in human females.

DESCRIPTION OF THE PRIOR ART

There has for many years been a need to predict, detect and diagnose the precise time of ovulation in a given female mammal.

For birth control purposes, the method of predicting the time of ovulation and abstaining from exposure to conception during the "fertile period" surrounding that ovulation is generally referred to as the "rhythm method". The "rhythm method" has not proven to be a reliable method of birth control, primarily due to the inability of prior art methods to give advance "notice" of the onset of the fertile period. The desirability of improving the reliability of this method need not be discussed at length.

Alternatively, it can be of great importance to determine the precise time of ovulation in order to ensure that fertilization occurs and that offspring are produced. This determination is useful to owners of pets, such as cats and dogs, as well as to breeders of livestock and particularly to breeders of thoroughbred race horses or cattle. While the prediction of ovulation is of importance in breeding animals; of even greater importance is the ability to predict whether and when a human female will ovulate so that her chances of producing desired offspring may be increased.

A. Diagnosis or Detection of Ovulation.

In addition to predicting or detecting the occurrence of ovulation, it may be very important to diagnose whether ovulation is indeed occurring. Heretofore, there has been no simple, inexpensive test by which a doctor may diagnose the occurrence of ovulation. Since the occurrence of vaginal bleeding may not be a reliable indicator that ovulation has indeed occurred, and since in many instances it would be desirable to begin treatment for a suspected condition without awaiting the onset of menstruation to determine that ovulation has, in fact, occurred, a need exists for a method to accurately diagnose the occurrence of ovulation at any stage in the menstrual cycle.

The occurrence of ovulation can be established with some certainty through various prior art methods. While the only irrefutable method of proving ovulation is the occurrence of conception (or occasionally the actual recovery of the egg), several testing techniques are available which may be used to presumptively confirm the occurrence of ovulation. At present, these tests can give a reasonably good indication that ovulation has or is just about to occur, however no simple, inexpensive technique is capable of reliably predicting ovulation more than a day or two in advance.

1. Surgical Techniques.

Surgical techniques for detecting ovulation either call for incisions to be made which facilitate the observation of the corpus luteum of the ovary for physical signs of ovulation, or require that attempts be made to recover the ovum from the ovaduct. Neither of these methods have gained widespread acceptance as simple, safe or reliable techniques.

2. Clinical Techniques.

Clinical evaluation has often been suggested as a method of detecting the time of ovulation. One such method focuses upon the appearance of pelvic discomfort at the time of expected ovulation. This "mittelschmerz" is thought to be brought about either by distention of the ovary or by peritoneal irritation from bleeding as a result of follicular rupture. Unfortunately, even among those patients who do experience "mittelschmerz" monthly, the symptom does not appear to be particularly related to the time of ovulation. Similarly, a mucoid vaginal discharge may sometimes be observed which is the result of increasing secretion from the cervix. This discharge may sometimes be noted immediately prior to ovulation and may be observed in conjunction with premenstrual mastalgia, slight edema or tension. While suggesting that ovulation is in fact occurring, the various techniques described above have proved of little value in precisely predicting or detecting the time of ovulation.

Perhaps the most popular and widely used method of detecting and timing ovulation is the use of graphic recording of the waking temperature at basal conditions. Using this method, an extremely dedicated woman with uniform daily habits can determine the time of ovulation within 2 days, after its occurrence. In recording the basal body temperature, a rise in temperature is commonly associated with the beginning of the luteal phase, but can vary from the actual time of ovulation by as much as 72 hours. A theoretical basal body temperature chart is shown in FIG. 1(a) and actual basal body temperature charts for four cycles are shown in FIGS. 2(a), 3(a), 4(a), and 5(a). Thus, at best, the basal body temperature can indicate the close of the fertile period.

3. Biochemical or Histological Techniques.

In more recent years, various biochemical and histological methods have been developed for detection of the precise time of ovulation. These methods include histologic evaluation of endometrial samplings, the use of diffferential staining techniques on vaginal desquamate and the measurement of hormonal levels throughout the menstrual cycle.

It has long been known that a normal menstrual cycle is accompanied by certain cyclic variations in the concentrations of certain hormones appearing in the blood. Generally, taking the day of ovulation to be day 0 (the point commonly referred to as being "midcycle"), estrogen levels normally begin to rise on approximately day −3, however in some women, may be found to rise as early as day −6, or even earlier. This pre-midcycle estrogen rise is followed by a sharp rise in lutenizing hormone, which is generally accepted to trigger ovulation. Shortly after ovulation, on day +2 or day +3, the level of progesterone begins to rise and remains at sustained levels until day +8 or day +10. The theoretical level of estrogens and progesterone are shown in FIG. 1(c) and actual levels for four different cycles are shown in FIGS. 2(c), 3(c), 4(c) and 5(c). The theoretical level of lutenizing horome (LH) is shown in FIG.

1(b) and the actual LH levels for 4 cycles are shown in FIGS. 2(b), 3(b), 4(b), and 5(b).

In humans, the preovulatory rise in serum estrogens coupled with a sharp rise in lutenizing hormones (LH) levels as determined by radioimmunoassay of serially drawn blood samples is perhaps the most accurate indicator of impending ovulation. Ovulation most likely occurs 12-24 hours after maximum LH levels. A subsequent rise and persistent high level of serum progesterone indicates that ovulation has occurred. Since these determinations are expensive and not widely available, other clinical parameters are used to predict the fertile period. These rely on various physical and biochemical changes, in the cervical mucous and vaginal mucosa caused by increasing estrogen levels. Each of these individual parameters shows substantial variability but as a composite they yield reliable results.

In recent years, certain other biochemical tests have been developed for the purpose of pinpointing the time of ovulation. One such test, referred to as the cervical mucous test, has been devised for the purpose of predicting the time of ovulation through the measurement of the concentration of glucose present in the cervical mucous. The basis for this test is that during the preovulatory phase, the cervical mucosa and the endometrium secrete glycogen and other polysaccharides to furnish an extrinsic source of energy for the anaerobic metabolism of the sperm and ovum, and of the conceptus during its 6 day journey into the uterine fluids. In order to monitor the concentration of cervical glucose, various tests have been proposed which involve the impregnation of a paper tape with various chemical means which respond to the presence of glucose. Since the concentration level of vaginal glucose differs significantly from that of cervical glucose, it has been necessary to minimize the contact of the impregnated paper tape with glucose found in the vagina itself. This requirement has lead to the development of plastic syringe-like instruments which shield the paper tape from the various vaginal secretions, and particularly vaginal glucose, while the syringe is brought into a position where its tip is in close proximity to tissues which are bathed only in cervical mucous. The syringe is then activated to expose the test tape to the cervical mucous, and contact is maintained for a sufficient length of time (often several minutes) to allow a color indication to take place. The test tape must then again be protected while the syringe-like instrument is removed so that it will not come in contact with undesired glucose in the vaginal secretions. Even if the additional precaution of an aqueous vaginal douche is employed, the possibility of contamination by vaginal secretions remains great, and therefore the reliability of the test is severely hindered. For this reason, the cervical mucous test must be performed by trained personnel (preferably a gynecologist) during an office visit. It then becomes possible to take precautions to ensure that the cervical mucous is properly sampled.

In instances where it is possible to obtain the proper sampling for the cervical mucous test, it has proved reasonably reliable in providing ovulation indicia which are accurate from within one to two days before, to one day after the actual occurrence of ovulation. Therefore, in spite of its clinical drawbacks, the cervical mucous test may prove to be valuable to infertile patients desiring to conceive. It is of little or no use however in avoiding conception, since conception may occur prior to any indication of ovulation.

Another test which has received some attention is the monitoring of salivary alkaline phosphatase levels which generally appear to parallel plasma estradiol (estrogen) levels. Unfortunately, the presence of alkaline phosphatase shows significant daily variations, not only between individuals but also within any given individual. Furthermore, this alkaline phosphatase test tends to provide its characteristic indication during a period ranging from one to ten days prior to the actual occurrence of ovulation. Due to this uncertainty, this test appears to be unreliable in predicting either the onset of the fertile period or the actual occurrence of ovulation.

4. Summary.

The following conclusions can be drawn concerning the state of the art in determining the precise time of ovulation in a human female:

1. Although surgical tests may prove to be reliable, they are not practical except on an occasional basis due to their deleterious side effects.

2. Of the chemical tests presently known to the art, the most reliable method of predicting the time of ovulation utilizes the graphing of hormone levels in blood plasma drawn at regular intervals throughout a menstrual cycle. By plotting the levels of lutenizing hormone (LH), estrogens and progesterone in blood plasma, it is possible to establish a good estimate for the time of ovulation. 3. At present, the most widely used technique for detection of ovulation utilizes the recording of basal body temperature. A sustained rise in basal body temperature provides a reasonably good indication that ovulation preceded the beginning of that rise.

B. Prediction of the Fertile Period.

It is generally accepted that the maximum survival function of spermatozoa capable of fertilizing an ovum is approximately 3 days following coitus. Although theoretically any coitus prior to ovulation entails a certain risk of pregnancy, as a practical matter, abstinence from sexual intercourse for the 3 days prior to ovulation is generally considered to be a "safe" period prior to the occurrence of ovulation. It is generally recognized that the ovum is susceptible to fertilization for a matter of hours. In the rabbit or rat, for example, there is a decreased fertility after the sixth hour. It is generally recognized that the human ovum is fertilizable probably for about 12 hours and certainly for no more than 1 day. The human fertile period, then, is up of no more than 4 days out of the entire menstrual cycle. If it were possible to accurately predict this fertile period, it would theoretically be necessary to either abstain from intercourse or use alternate birth control methods only for that 4 day "fertile period" rather than for the entire menstrual cycle. Heretofore, the only widely used technique for predicting the fertile period of a female has been the method which relies upon basal body temperature determination of ovulation in a plurality of preceding cycles to determine the expected time of ovulation for future cycles. This method is not really directed to ascertaining the precise fertile period for a given cycle, but rather is intended to establish a statistically "dangerous" period during which coitus is likely to produce pregnancy. Since this information is based upon past performance, and since the time of ovulation varies markedly between different individuals as well as between cycles of a given individual, the period for abstinence must be long enough to considerably reduce the possibility of pregnancy.

One method for calculating the period for abstinence which has been suggested is that intercourse be avoided beginning at the time of menses and continuing until a sustained rise in basal body temperature has been observed. Alternatively, a patient may record 12 previous consecutive cycles, noting the longest and shortest cycles experienced during this interval. Since it is generally agreed that menses usually occurs about 14 days after ovulation, it has been suggested that the fertile period in a given cycle is between 18 and 11 days before menstruation. Using this period as the fertile period, the period for abstinence may be calculated by subtracting 18 days from the number of days of the shortest recorded cycle to determine the first unsafe day and by subtracting 11 days from the longest recorded cycle to arrive at the last unsafe day. Since an extremely regular woman would usually have a cycle which varies in length between 26 and 30 days, the shortest period of abstinence would be expected to range from day 8 to day 19, or more than one-third of the total cycle. It has been estimated that only 55% of the naturally occurring menstrual cyles are within the range of 25 to 31 days, and that even the most regular of women may have cycles which vary from 21 to 33 days. Consequently, it may be concluded that the irregularity and extreme length of the required period of abstinence makes the rhythm method based on basal body temperature and statistical prediction unacceptable to all but the most regular and dedicated of women.

Of the various techniques for detecting ovulation which have been considered above, none of these techniques have the practical capability of predicting the onset of ovulation sufficiently in advance to allow the prospective calculation of the period of abstinence. While certain of these tests may occasionally predict ovulation up to 10 days in advance of its occurrence, all of these tests are equally as likely to give no indication of ovulation until after the onset of the fertile period. This irregularity further precludes any possibility that the tests which do predict ovulation in advance could be used to shorten the period of abstinence since their irregularity would result in periods of abstinence which show no better statistical significance than those based upon the natural occurrence of menstruation. The relative failure of the various techniques discussed above to predict the fertile period in advance has lead one commentator to conclude:

"The possibility of predicting ovulation by 3–4 days, and thus providing a couple with a period of abstinence no greater than 5 days is intriguing. John Rock, for one, views this approach with some optimism. Should such a method finally be worked out, it would be but another addition, albeit a vital one, to our armamentarium for controlling the population growth of the world. Certainly, in many nations and even among many couples in our own country, much education would be required to convince the male that he should abstain, even for so short an interval as 5 days, and mush effort would have to be expended before some males could look upon this as anything but an infringement of their rights as husbands and lovers. It is clear, nevertheless, that if we could find a way to predict ovulation, we would provide a very natural means of family spacing—in fact, the most physiologic menas imaginable. Even if it should require somewhat greater effort then the other methods now available, it would be a real boon to many people, regardless of their religious affiliation. It should be kept in mind that even taking a pill once a day requires some effort and intelligence, and certainly the mechanical contrivances now available are, to say the least, inconvenient."to a ("The Present Status of Rhythm Techniques", Luigi Mastroianni, Jr., M.D., Clinical Obstetrics and Gynecology, Volume 7, No. 3, 1964, pages 874–875).

SUMMARY OF THE INVENTION

Applicants have found that by monitoring the concentration of any of a number of volatile organic compounds commonly found in vaginal secretions, a reliable diagnostic indication of ovulation may be obtained. Certain of these compounds may also provide such indication in advance of the onset of the fertile period, thereby providing a method for increasing the reliability of the "rhythm" method of birth control. Unlike prior art methods, the present invention provides a simple, reliable home-test method for predicting, detecting or diagnosing ovulation.

There is a possibility—albeit remote—that odors produced and emitted by humans may play some subtle and as yet unknown role in human reproductive biology. Along with the anecdotal information in the literature, the scientific reports of certain respected researchers have stimulated speculation on this probability. These researchers reported that short chain aliphatic acids ($C_2$–$C_5$) found in the vaginal secretions of estrus female rhesus monkeys acted to induce mating by sexually active male rhesus monkeys. This has been used as the starting point for reports and speculations concerning the role these acid compounds might play in humans. Since some of the speculation has centered upon human vaginal secretions being a probable carrier of human chemical communication, knowledge of the nature and abundance of the small acids as well as other volatiles in this secretion may provide some facts on which to judge the current speculations. Consequently, this theory could explain the regularity with which the abundance of the volatile materials found in these secretions is seen to vary. While primarily under sex steroid control, upon excretion from the body, these compounds may be actively or vestigially targeted at the olfactory organs.

Generally, the method of the present invention comprises the steps of monitoring vaginal secretions for the concentration of at least one volatile organic compound having a molecular weight of between 50 and 350 grams per mole, by providing an indicator means for qualitatively and quantitatively responding to the concentration of said organic compound, whereby the means for indicating that concentration diagnoses the occurrence of ovulation in that menstrual cycle. The volatile organic compounds commonly occurring in vaginal secretions of women which are included in this molecular weight range may be seen in Table I.

TABLE 1

| ORGANIC CONSTITUENTS OF HUMAN VAGINAL SECRETIONS | | | |
| --- | --- | --- | --- |
| ALIPHATIC ACIDS | M.W. | HYDROXY-ACIDS | M.W. |
| Acetic | 60 | Lactic | 90 |
| Propanoic** | 74 | | |
| N-Butyric** | 88 | HYDROXY-KETONES | |
| Isobutyric** | 88 | | |
| Isovaleric** | 102 | 3-Hydroxy-2-butanone | 88 |

TABLE I-continued

| | | | |
|---|---|---|---|
| 2-Methylbutyric** | 102 | 2-Hydroxypropanone* | 74 |
| Valeric** | 102 | | |
| Myristic | 228 | AROMATIC COMPOUNDS | |
| Isomyristic | 228 | | |
| Pentadecanoic | 242 | a) Aldehydes | |
| Isopentadecanoic | 242 | Benzaldehyde** | 106 |
| Palmitic | 256 | Phenylacetaldehyde | 120 |
| Palmitoleic | 254 | Furfural* | 96 |
| Steric | 284 | | |
| Oleic | 282 | b) Alcohols | |
| Linoleic | 280 | Phenol | 94 |
| | | p-Cresol | 108 |
| ALCOHOLS | | Furfuryl Alcohol | 98 |
| | | c) Acids | |
| | | Benzoic | 122 |
| N-Dodecanol | 186 | | |
| N-Tetradecanol | 214 | d) Nitrogen Containing | |
| N-Hexadecanol | 242 | Pyridine | 79 |
| N-Octadecanol | 270 | Indole | 117 |
| | | LACTAMS | |
| GLYCOLS | | | |
| | | 2-Piperidone** | 99 |
| Propylene Glycol | 76 | | |
| Ethylene Glycol | 62 | | |
| Glycerol | 92 | SULFUR CONTAINING | |
| | | Dimethylsulfone | 94 |
| | | MISCELLANEOUS | M.W. |
| | | N-Heptadecane | 240 |
| | | Cholesterol | 386 |
| | | Squalene | 410 |
| | | Urea | 60 |

*Not consistently present in detectable amounts in all subjects.
**Consistently present in detectable amounts in only 3 subjects.

Additionally, the method of the present invention generally comprises the steps of monitoring vaginal secretions for the concentration of urea and providing an indicator means for qualitatively and quantitatively responding to the concentration of urea, whereby the means for indicating that concentration diagnoses the onset of the fertile period, the maximal preovulatory estrogen rise, and/or the time of ovulation.

The method of the present invention further comprises a method whereby one or more volatile organic compounds and/or urea are monitored by an indicator means qualitatively and quantitatively responding to each of the compounds whereby the means for indicating the concentration of these various compounds diagnoses the occurrence of a given point in the menstrual cycle.

Although the present invention is primarily intended for use by human females, it is also equally applicable to other female mammals, and particularly to domestic cattle, horses, cats and dogs. In the breeding of these animals, it is of primary importance to determine the fertile period of a given female animal so that access to a male need be provided for the shortest length of time. This is particularly true of horses where stud service fees are involved and where the prediction of the fertile period of the female animals will allow for the more efficient utilization of each stud animal.

In a first preferred embodiment of the present invention, lactic acid is monitored by an indicator means which responds qualitatively and quantitatively to the concentration of the lactic acid through a color change reaction. In this preferred embodiment, a binder or carrier is impregnated with chemicals which respond with a color change reaction when exposed to lactic acid. In monitoring the concentration of lactic acid, a first increase in concentration of lactic acid occurs just prior to the rise in serum estrogens, or approximately 4 days prior to the time of ovulation, thereby indicating the onset of the fertile period of that female. At least 4 days after that increase, a second lactic acid increase indicates the time of ovulation. 24 to 36 hours after this second "ovulatory" increase, coitus will not result in conception. Therefore, the present invention defines a fertile period lasting at least 5 days, during which conception would be possible.

While the lactic acid embodiment of the present invention is primarily intended to predict the onset of the fertile period so that conception may be avoided, once the fertile period is accurately predicted, it is obviously also useful in aiding in producing the conception of offspring.

At the present time, experimental data indicates that the lactic acid embodiment of the present invention would be useful as a birth control method in approximately 80% of the human female population. Since this method utilizes naturally occurring secretions which, if desired, may be tested after being removed from the body, its use entails no adverse physiological side effects. This 80% figure represents a very substantial advance over the old "rhythm" method and compares favorably to the statistics for other popular methods, many of which are likely to produce undesirable side effects.

In a second preferred embodiment, acetic acid is monitored for the purpose of determining and diagnosing the occurrence of ovulation. A first increase in concentration of acetic acid appears at or just after the time of ovulation, and a second increase occurs during the luteal phase. Applicants have found that the cyclical nature of acetic acid concentrations would be expected to appear in at least 80% of all menstrual cycles. Since concentration maxima do not occur prior to the time of ovulation, this preferred embodiment is particularly useful for diagnosing the time of ovulation, and may be coupled with the lactic acid embodiment discussed above to provide confirmation of the occurrence of ovulation.

In a third preferred embodiment of the present invention, urea is monitored by an indicator means which responds qualitatively and quantitatively to the concentration of urea present through a color change reaction. In monitoring the concentration of urea, a first increase in concentration occurs prior to the rise in serum estrogens, or approximately 5 to 6 days prior to the time of ovulation, thereby indicating in advance the onset of the fertile period of that female. Additionally, this first increase in the concentration of urea would be expected to precede, by approximately 24 to 48 hours or be coincidental with the first increase in concentration of lactic acid, thereby providing somewhat more advanced notice of the onset of the fertile period than that provided by lactic acid. At least 4 days after that first increase in urea concentration, a second urea increase is seen which occurs from 48 hours before to coincidental with the time of ovulation. Since it is well known that serum estrogens peak from approximately 48 hours before to coincidental with the time of ovulation, this second urea rise is of particular use to couples desiring to conceive offspring. Similarly, its accurate forecast of impending ovulation allows its utilization in defining the fertile period in a manner similar to that employed for lactic acid and/or other relatively small volatile organic compounds in order to produce a reliable birth control method. As such, abstinence from coitus beginning approximately 24 hours after the first increase in urea concentration and extending until approximately 48 to 72 hours after the second increase in urea concentration would be expected to define an acceptable period lasting approximately 5 to 6 days, during which conception would be possible.

The statistical reliability of the present invention may further be improved by determining in advance whether its use is practical for a given woman. This can be accomplished by coupling the use of the indicating means of the present invention with one of the known methods of predicting ovulation, thereby standardizing the use of the present invention for a given female's individual body chemistry.

In the preferred embodiments of the present invention, the indicator means may consist of various compounds which are impregnated in a suitable binder or carrier such as a strip of filter paper, a feminine tampon, or any other chemically inert binder which may be brought into contact with vaginal secretions to produce a desired indication, such as color change. It is anticipated that these chemically impregnated binders be standardized for color so that a woman may accurately determine the concentration of the volatile organic compound to be detected. In the case of lactic acid detection, for example, this binder would be impregnated with chemicals which produce a bright yellow color when exposed to lactic acid, the intensity of that color varying in accordance with the concentration of lactic acid present. In the case of urea detection, a somewhat more sophisticated indicator means is employed in which a linear color change reaction is utilized to determine the concentration of urea present. Alternatively, gas chromatographic indicator means may be employed.

Thus, it can be seen that one object of the present invention is to provide a method of reliably diagnosing ovulation in a female mammal. A second object of the present invention is the prediction of the fertile period of a female mammal. A further object of the present invention is the provision of a simple "home-test" method for diagnosing ovulation. Another object of the present invention is the provision of a simple "home-test" method for predicting the fertile period. One aim of the present invention is the provision of indicator means for qualitatively and quantitatively responding to the concentration of at least one volatile organic compound commonly occurring in the vaginal secretions of female mammals. Another aim of the present invention is to provide a chemically inert binder which is impregnated with chemical means for producing a color change in response to certain given conditions. These and other objects of the present invention will become apparent from the description of the preferred embodiments which appear herein.

DESCRIPTION OF THE PREFERRED EMBODIMENT

Figure 1:
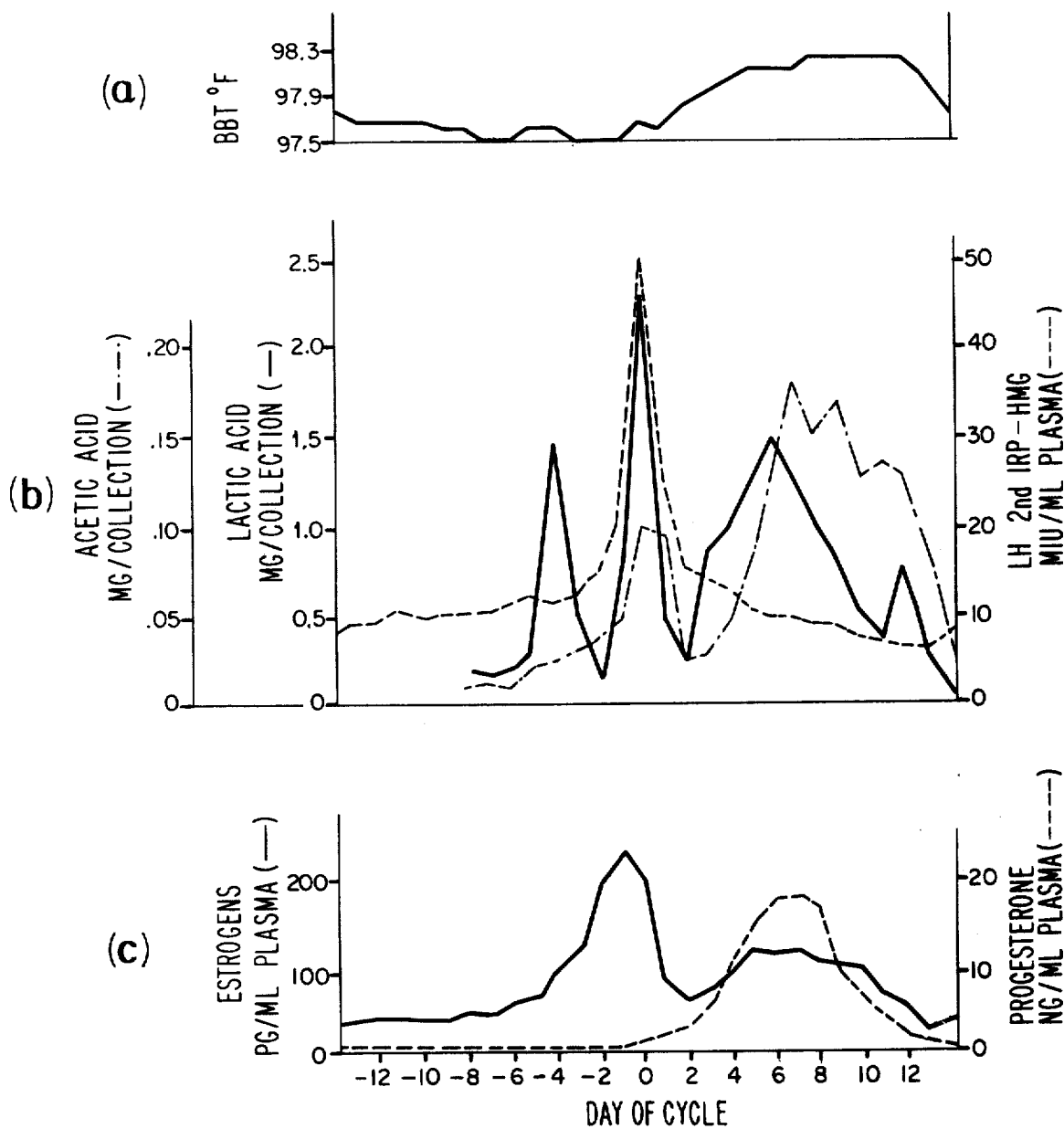
FIG. 1 is a graph showing the theoretical values of basal body temperature, progesterone, lutenizing hormone, estrogens, lactic acid, and acetic acid over the course of one menstrual cycle.

Although specific forms of the invention have been selected for illustration in the drawings, and the following description is drawn in specific terms for the purpose of describing these forms of the invention, this description is not intended to limit the scope of the invention which is defined in the appended claims.

Vaginal secretions are thought to consist of several components; (a) vulval secretions from sebaceous, sweat, Bartholin's and Skeen's glands, (b) mucus secretions from the cervix, (c) endometrial and oviductal fluids, (d) transudate through the vaginal walls, and (e) exfoliated cells of the vaginal mucosa. The type and amounts of (b), (c), and (e) are known to be influenced by biochemical processes which are dependent on sex steroid levels; consequently, metabolic by-products of these processes should also vary with sex steroid levels. Using gas chromatography (gc) and combination gas chromatographymass spectrometry (gc-ms), applicants have investigated changes in the nature and abundance of volatile chromatographable compounds found in the vagina during the menstrual cycle. Such changes could predict, detect or diagnose changes in circulating hormone levels and thus be diagnostic of ovulation or the fertile period. Predicting either ovulation or this fertile period via these readily accessible metabolites has led to the development of a simplified diagnostic aid for use by the clinician or the individual trying to maximize or minimize the changes of conception.

Applicants found that lactic acid is the major acidic constituent in human vaginal secretions during the time of ovulation and that the amount of it present in the secretion varies with sex steroid levels. Acetic acid is the only small aliphatic acid consistently present in large amounts in most subjects. Similarly, urea was consistently found to cycle in correspondence to sex steroid levels.

Referring to FIG. 1, the theoretical lactic acid curve showing the concentration of lactic acid is plotted over a single menstrual cycle. The variations and concentration of lactic acid can be compared to the variations in basal body temperature, progesterone, estrogen, and acetic acid. FIG. 1 demonstrates that, if the time of ovulation is considered to be day 0, the concentration of lactic acid should theoretically peak first on day −4 which is seen to be approximately one day before the preovulatory estrogen rise, and is seen to increase a second time at the time of ovulation, or day 0. A third less dramatic increase in lactic acid concentration appears in the postovulatory phase of the cycle. No corresponding increase in lactic acid concentration is expected in the preovulatory phase except that increase which directly precedes the onset of the fertile period.

The information provided for lactic acid concentrations in FIG. 1 is consistent with the experimental data which has resulted from applicants' research. While the preovulatory increase in lactic acid would be expected to occur on day −4 in most women, this preovulatory increase appears to consistently precede by approximately 1 day the preovulatory estrogen rise. While this preovulatory estrogen rise normally begins on day −3 in some women, it may occur as early as day −6 and even, upon occasion, earlier. Thus, strictly speaking, the preovulatory lactic acid increase, which precedes the preovulatory estrogen rise, could occur between day −4 and day −7, or perhaps even earlier. In no instance known to applicants has the preovulatory lactic acid rise occurred later than the preovulatory estrogen rise, thereby indicating that this first lactic acid increase will always occur prior to the fertile period, however in some women its occurrence will precede the onset of the fertile period by more than one day.

Figure 5:
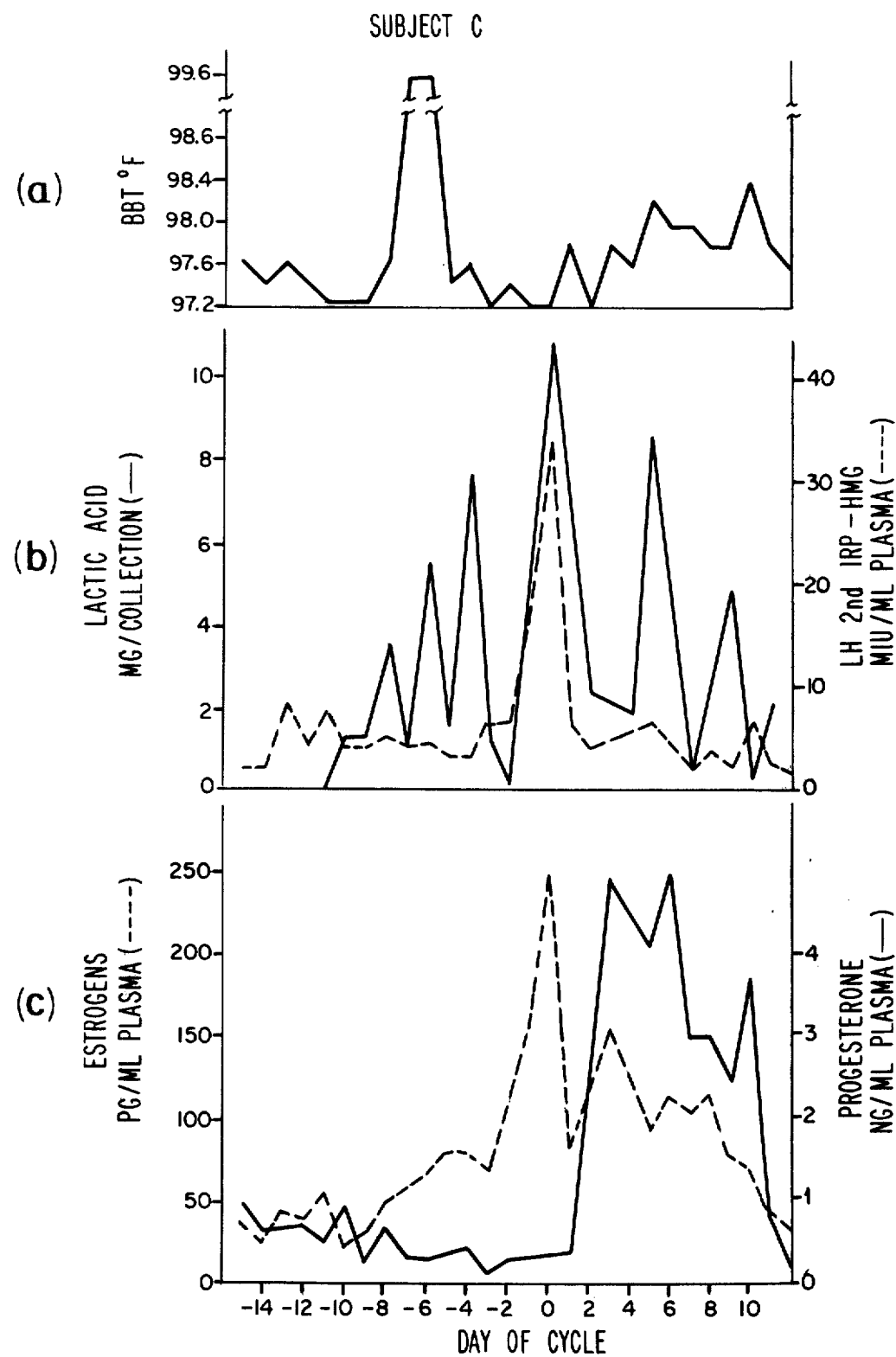
FIG. 5 is a graph of the experimental data for basal body temperature, lutenizing hormone, progesterone, estrogens, and lactic acid as determined for a first cycle of a thrird subject.

The increase in lactic acid concentration which is observed at the time of ovulation would similarly be expected to vary somewhat from woman to woman. While at no time would it be expected that this midcycle or ovulatory rise in lactic acid would differ from the actual time of ovulation by more than 2 days, it would be expected that the characteristic for this rise would be reasonably uniform within the various menstrual cycles of a given woman. As previously discussed, it would not be expected that the method of the present invention would be applicable to 100% of the women who might wish to employ this method. The cycle of subject C, shown in FIG. 5, is included as an example of an expected type of variation found in a minority of women to whom this method would not generally apply. Therefore, it would be suggested that a given woman could determine the applicability of the method of the present invention to her by utilizing it with one of a number of other known ovulatory indicators, or, alternatively, with the acetic acid preferred embodiment of the present invention, or with one of the other embodiments of the present invention so that a positive correlation of test results could reassure her of the operability and applicability of the present invention to her individual body chemistry.

EXAMPLE 1

Secretions were collected during 22 menstrual cycles from seven healthy, ovulating women. Ovulation was documented in four cycles using radioimmunoassays. In the rest, the day of maximum LH levels (henceforth day 0) was estimated from basal body temperature (BBT) charts. The subjects were asked to record incidents of sexual arousal or coitus and not to use vaginal deodorants or douches. No other restrictions were placed on daily habits or diets.

Pre-cleaned tampons were used for secretion collection. They were inserted before the subject went to sleep and removed the next morning. Beginning 1 or 2 days after the end of menses, samples were collected each night for 10 or 12 consecutive nights, and every other night thereafter until the start of the next menses.

Organic materials were extracted from the tampons by a continuous 24 hour extraction using dichloromethane. Each extract was concentrated to approximately 250 $\mu$l via rotary evaporation at room temperature. Chromatography was performed using internal and co-injected standards. Combination gc-ms was carried out at the Monell Chemical Senses Center on selected samples with identifications confirmed by comparison of mass spectra and gc retention times with those from commercially available samples.

In 20 of the 22 cycles studied, lactic acid reached its highest or second highest value within 2 days of the predicted or determined day of ovulation. Eighteen of the 22 cycles showed a second increase in lactic acid concentration which occurred from 3 to 6 days before the midcycle lactic acid peak. Studies of this and other data indicate that this midcycle lactic acid peak closely corresponds to the actual time of ovulation, and it can be seen that in more than 80% of the cycles, the preovulatory increase in lactic acid concentration occurred immediately prior to the onset of the fertile period.

EXAMPLE 2

In a second series of tests (also conducted at the Monell Chemical Senses Center), blood hormone levels were plotted for four different cycles selected at random from the twenty-two cycles referred to above. In three or four of these cycles, the pre-midcycle (pre-ovulatory) increase occurred one day before estrogens began to rise. FIGS. 2, 3, 4 and 5 show the four cycles where lactic acid production was plotted with circulating levels of estrogens, progesterone and LH. The pre-midcycle increase occurred one day before estrogens began to rise in three of the four cycles where blood hormone levels were determined.

FIGS. 2–5 show that the midcycle peak in lactic acid coincides very closely with the midcycle estrogen rise and the LH surge. Maximal amounts of lactic acid varied from subject to subject.

Figure 2:
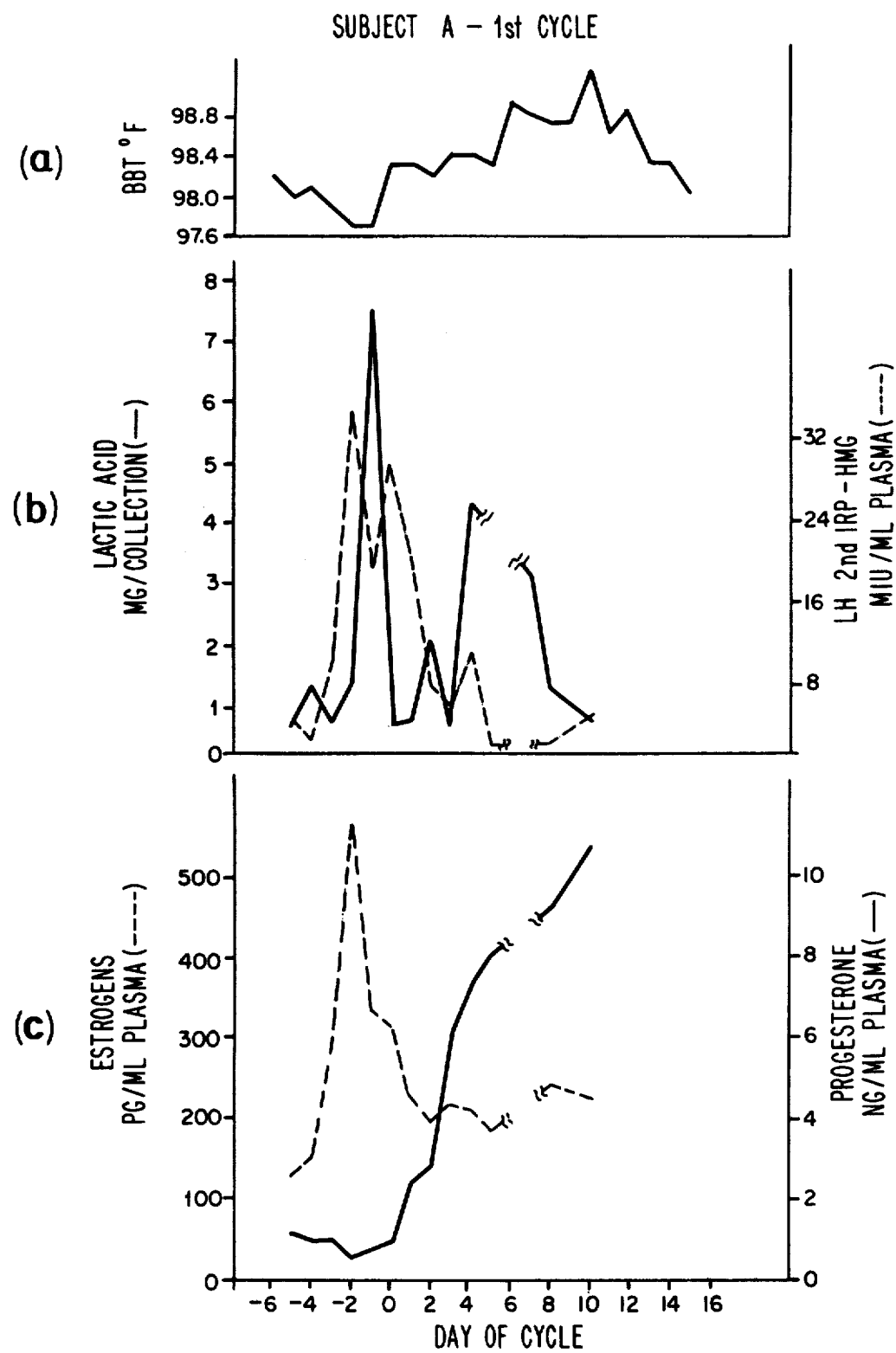
FIG. 2 is a graph of the experimental data for basal body temperature lutenizing hormone, progesterone, estrogens, and lactic acid as determined for a first cycle of a first subject.
Figure 3:
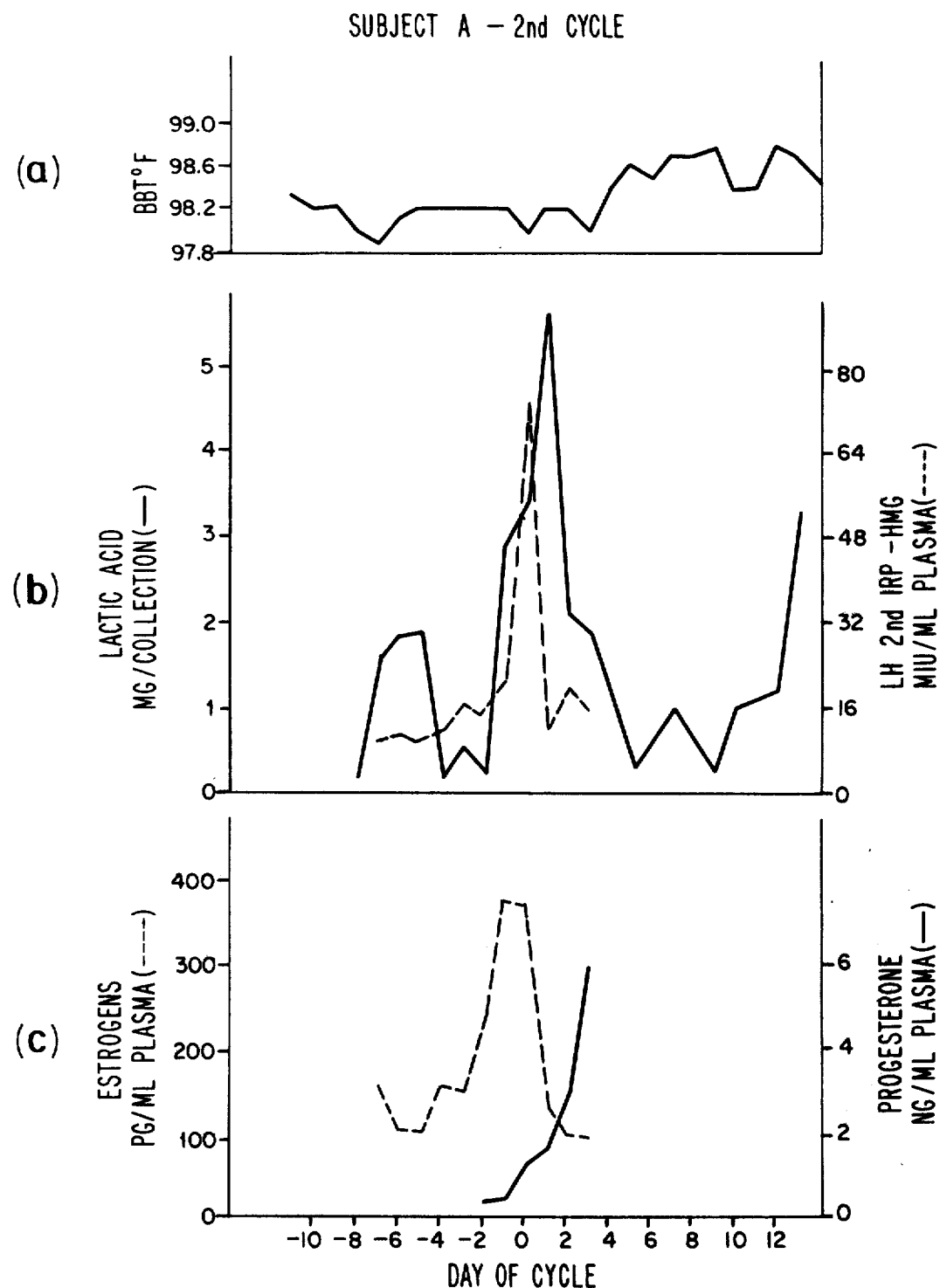
FIG. 3 is a graph of the experimental data for basal body temperature, lutenizing hormone, progesterone, estrogens, and lactic acid as determined for a second cycle of the first subject.
Figure 4:
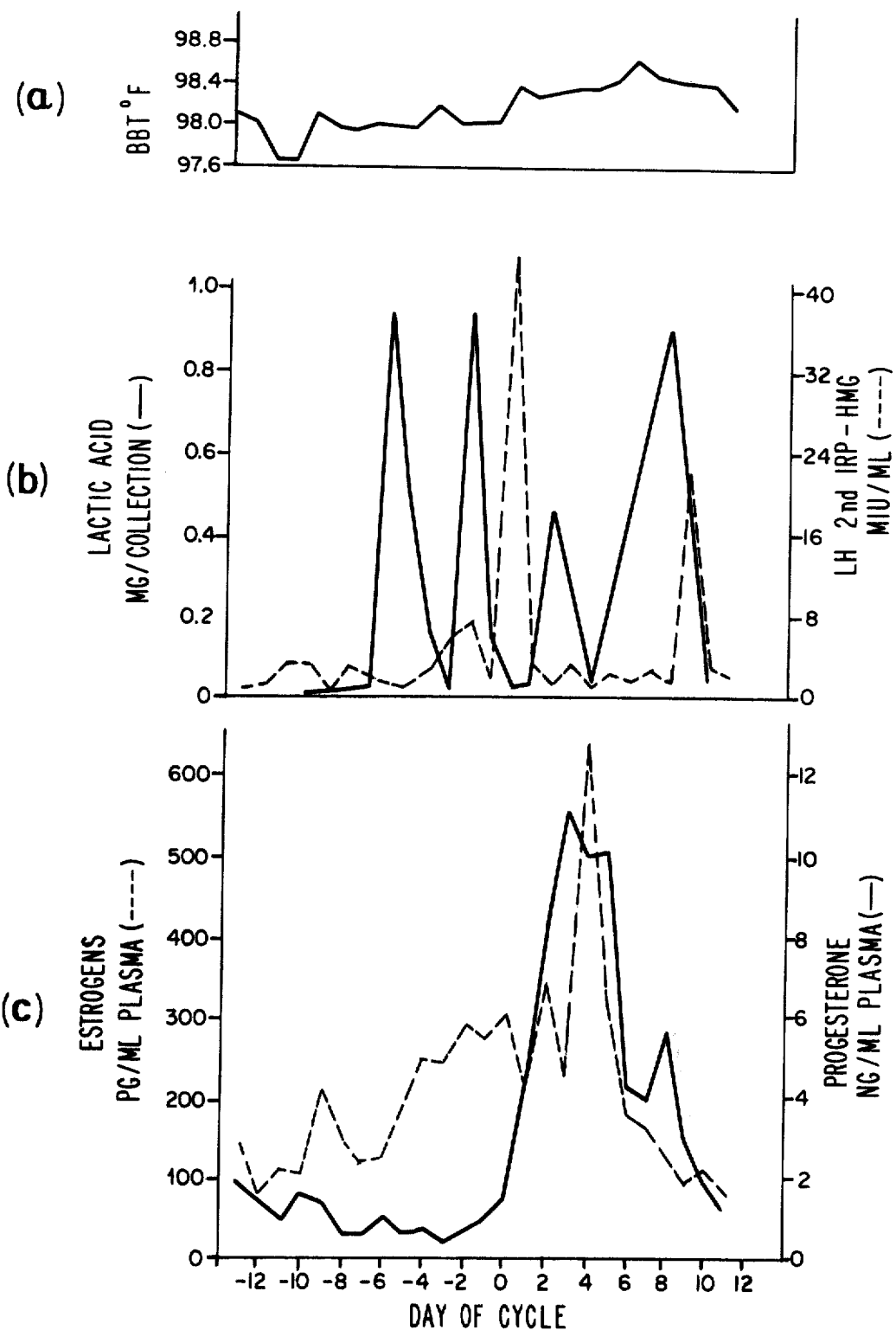
FIG. 4 is a graph of the experimental data for basal body temperature, lutenizing hormone, progesterone, estrogens, and lactic acid as determined for a first cycle of a second subject.

Each of the cycles from subject A seen in FIGS. 2 and 3 show a small rise in lactic acid concentration just before blood estrogens begin to rise. This pre-midcycle rise is much more evident in subject B (FIG. 4). Subject C (FIG. 5) shows three rises and falls in lactic acid concentration during the slow rise in blood estrogens from days −9 through −4. The last and largest of these rises precedes the sharp increase in estrogens on day −3. This subject showed the greatest variability in daily lactic acid throughout each of her five cycles.

All cycles in the figures as well as 14 of the remaining 18 cycles show a decrease in lactic acid after midcycle. The second half (luteal phase) of the cycles shows rises in lactic acid which seem to agree with increasing and/or maximum progesterone levels and the luteal phase estrogen rise. However, late luteal rises in lactic acid seen in three of the cycles appear to coincide with the drop in the steroid levels characteristic of this part of the cycle.

The amount of lactic acid collected did not appear to depend upon the amount of secretion collected. In 14 cycles where weights were recorded, maximum amounts of lactic acid coincided with the maximum quantity of secretion in only two cycles.

EXAMPLE 3

The acetic acid preferred embodiment also has yielded data indicating that it is a reliable diagnostic test of ovulation.

Referring to FIG. 1, the typical concentration of acetic acid which would be expected to occur over the course of one menstrual cycle is plotted in FIG. 1(b). A first acetic acid rise is seen to occur at or shortly after the time of ovulation. A second rise is seen to occur between +6 and day +8. As with the lactic acid graph shown in FIG. 1, the various results for acetic acid may be expected to vary from woman to woman, however the pattern shown in FIG. 1 is consistent with the experimental data produced by applicants' research. Approximately 80% of the cycles tested by applicants showed a cyclical variation of this kind. Once again, a woman would be expected to determine the reliability of an acetic acid test and its applicability to her individual body chemistry by monitoring the concentration of acetic acid and correlating that concentration with other diagnostic ovulatory tests.

Presence of acetic acid was determined in 20 cycles. In 16 of these, the acid varied in a cyclical manner displaying two concentration maxima: one around mid-cycle, the second, during the luteal phase. Maximum amounts varied from 0.070 mg in subject B to 0.610 mg in subject D. The four cycles shown in the figures had maxima which occurred on or after day 0.

Higher acids ($C_3$-$C_5$) were confirmed to be present in only two subjects (D and F). Subject D displayed $C_3$-$C_5$ acids only in the luteal phase of 3 cycles and from day 0 through the luteal phase in a fourth cycle. Subject F showed these acids present almost every day in one cycle with maximal amounts present on day −1. The remaining subjects displayed chromatographic peaks near the correct retention times for n-butyric and iso-valeric/ α-methylbutyric acids (these two co-eluted); however, mass spectra taken at various times in each subject's cycles showed these peaks contained no detectable amounts of acids.

Thus, it can be seen that the presence of acetic acid may be useful in predicting the time of ovulation, whereas higher acids are not commonly found in the vaginal secretions of most women. At present, there is some indication that when the longer chain acids do occur, they may occur in maximal concentrations at about the time of ovulation.

Figure 6:
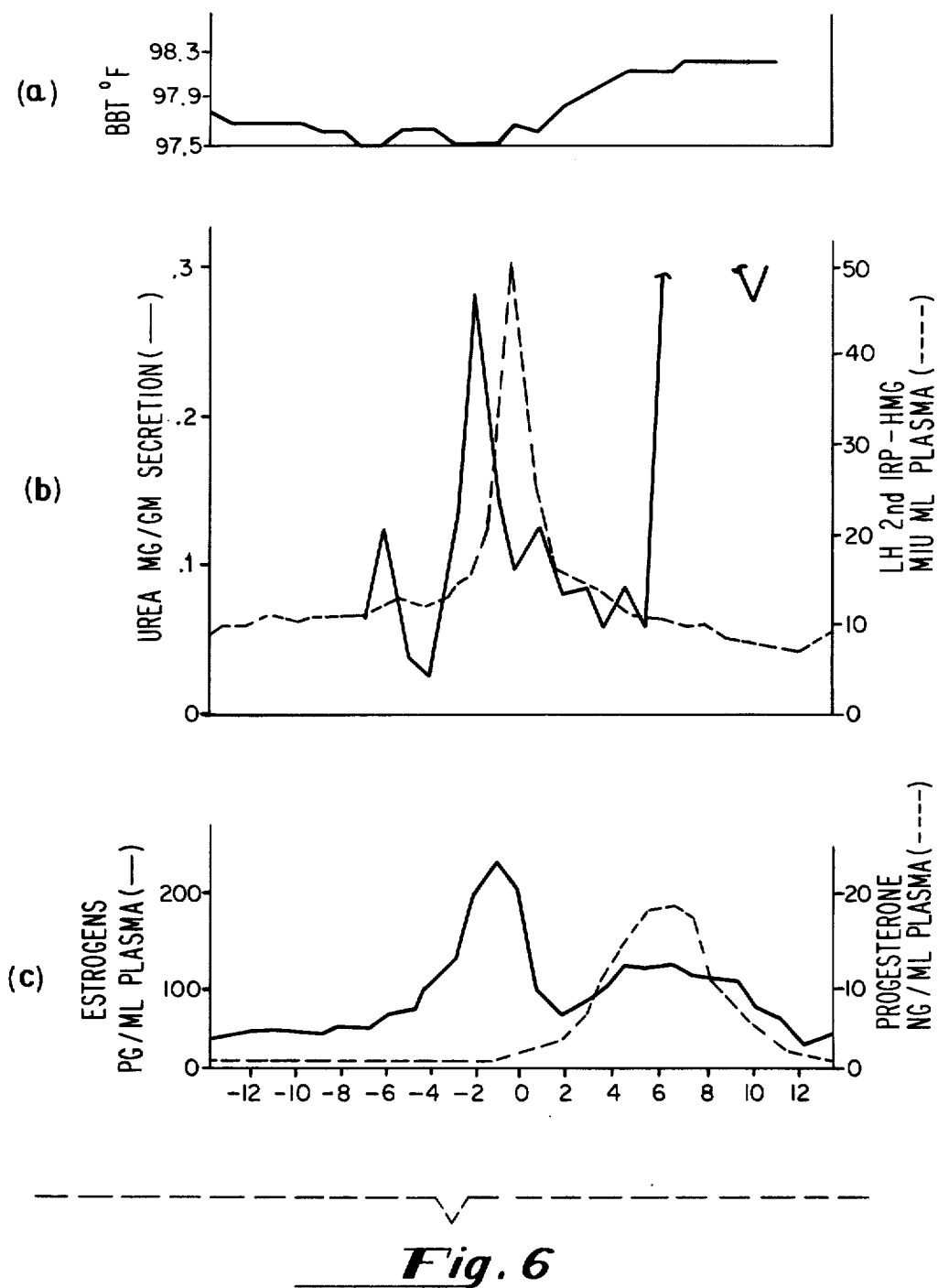
FIG. 6 is a graph showing the expected values of basal body temperature, progesterone, lutenizing hormone, estrogens, and urea over the course of one menstrual cycle.

Referring now to FIG. 6, the expected urea curve showing the concentration of urea is plotted over a single menstrual cycle. The variations in concentration of urea can be compared to the variations in basal body temperature, progesterone, and estrogen. FIG. 6 shows that, if the time of ovulation is considered to be day 0, the concentration of urea would be expected to peak first on approximately day −6 which is seen to be 2 to 3 days before the preovulatory estrogen rise shown in FIG. 6(c). FIG. 6(b) also indicates that the concentration of urea would be expected to increase a second time at approximately day −0, and that this second increase corresponds closely to the peak estrogen levels and the LH surge as plotted in FIG. 6(c). A third even more dramatic increase in the urea concentration appears in the postovulatory phase of the cycle, beginning at approximately day +6 and extending to menstruation.

The information provided for urea concentration in FIG. 6 is consistent with the experimental data which has resulted from applicants' research. Urea concentrations are generally expected to respond in a manner similar to that of lactic acid. While the preovulatory increase in urea would be expected to occur on day −6 in most women, this preovulatory increase appears to consistently precede by approximately 2-3 days the preovulatory estrogen rise. While this preovulatory estrogen rise normally begins on day −3 in some women, it may occur as early as day −6 and even, upon occasion, earlier. Thus, strictly speaking, the preovulatory urea increase, which precedes the preovulatory estrogen rise, could occur between day −6 and day −9, or perhaps even earlier. In no instance known to applicants has the preovulatory urea rise ever occurred later than either the preovulatory lactic acid rise or the preovulatory estrogen rise, thereby indicating that this first urea increase will always occur prior to the fertile period, however, in some women its occurrence will precede the onset of the fertile period by as much as perhaps 2 days.

The increase in urea concentration which is observed to coincide with the peak levels of serum estrogens would similarly be expected to vary somewhat from women to women, depending most probably upon the particular day in the cycle at which those serum estrogens will hit their maximal levels. In addition to the other advantages provided by the urea embodiment of the present invention, it should be noted that one significant advantage of the urea embodiment of the present invention is the ability to obtain accurate "spikes" during both the preovulatory and ovulatory increases. This is particularly important in light of the fact that in many women the preovulatory estrogen rise is not as precipitous as that plotted in FIG. 6)c), but rather is a gradual rise which may begin, in some cases, as early as day −10, and may be subject to some fluctuation prior to hitting its peak preovulatory level. Additionally, it would be expected that the characteristics for this rise would be reasonably uniform within the various menstrual cycles of a given woman. Although, as with the other substances previously discussed, it would not be expected that the urea embodiment of the present invention would be applicable to 100% of the women who might wish to employ this method, nonetheless, its reliability would be expected to be of the same order of magnitude as the two embodiments previously discussed. As before, it would be suggested that a given woman could determine the applicability of the method of the present invention to her by utilizing it with one of a number of other known ovulatory indicators, or, alternatively, with one of the other embodiments of the present invention so that a positive correlation of test results could assure her of the operability and applicability of the present invention to her individual body chemistry.

EXAMPLE 4

Secretions were collected during 14 menstrual cycles from healthy ovulating women. Each of the subjects wore a tampon for 6 hours during normal daily activity. After the end of a menses (1 or 2 days), samples were collected each day for 10 or 12 consecutive days and every other day thereafter until the start of the next menses. In addition to recording basal body temperature for each of the cycles, circulating hormone levels were plotted for 3 of the 14 cycles to determine the precise time of ovulation. Using methods for evaluation substantially similar to those described for Example 1, except as noted above, a comparison of the data obtained for these cycles indicated that a first urea rise would be expected between day −6 and day −5 in most subjects. Similarly, a second more dramatic rise, was found to occur slightly before the time of ovulation, generally coinciding with the maximal levels of serum estrogens. Several luteal rises were observed in various subjects, with the highest urea levels being obtained from day +6 through +12 in most subjects.

In addition to the identifications of lactic acid, acetic acid, and urea, the organic compounds found in Table I have also been unambiguously identified. Tentatively identified from its mass spectra or gc retention time is n-octadecanol. The quantities of each of these substances varied from subject to subject.

Lactic acid has been known to be present in and assumed to the principal cause of vaginal acidity since the work of Zweifel. This acid is thought to arise, at least in part, by the action of the lactobacillus of Doderlein on vaginal glycogen and/or simpler carbohydrates found in vaginal secretions. Vaginal glucose increases under the influence of estrogen, however, opinions differ as to whether vaginal glycogen actually increases or undergoes a rapid turnover because of estrogen. In either case, estrogens produce increases in carbohydrates available to microflora. However, it is difficult to account for the pre-midcycle and the often seen late luteal rise solely on the basis of increased carbohydrates in the vaginal secretion.

The rapid decreases in lactic acid after midcycle could be due to increased alkaline cervical mucus making its way into the vagina. Semen may also neutralize the vagina and this may account for some of the sharp decreases in lactic acid; however, subject C, who displayed numerous precipitous dips and rises in lactic acid amounts throughout the study denied having intercourse while she was a subject.

Acetic acid present in the vagina may be formed by the same microbial processes which produce lactic acid. The presence of higher acids in only two subjects suggests that conditions conducive to their production in large amounts are not present in all women.

The data presented above was obtained utilizing highly sensitive analytical instrumentation, such as a gas chromatograph, as an indicator means. This type of indicator means has never before been used in a thorough study of human reproductive tract secretions. Use of this instrumentation has offered new approaches in determining hormonal changes via analysis of simple metabolic end products.

In addition to determining the characteristic concentrations of volatile organic compounds which are present in vaginal secretions, the present invention also provides for chemical indicator means which respond to the concentration of compounds to be detected, thereby allowing for a reasonably precise prediction of the number of expected days prior to or after the occurrence of ovulation.

In the case of lactic acid, the indicator means may be produced as follows:

A chemically inert binder or carrier, such as a strip of analytical grade filter paper, is successively dipped into the following reagents: (a) 0.5M glucose buffer adjusted to pH 8.8 with sodium hydroxide and containing 0.4 molar semicarbazide (aminourea); (b) 0.027M DPN (diphosophopyridine nucleotide); (c) 3% solution perchloric acid; and (d) a solution containing 2 milligrams of L(+) lactic dehydrogeneous per 1 milliletter of distilled water. Upon exposure to as little as 10—20 micrograms of lactic acid, a bright yellow color is observed (within one minute), the intensity of that color varying according to the amount of lactic acid present.

An alternative method for producing such an indicator means for lactic acid is to impregnate the chemically inert binder with a solution of 0.4M solution of semicarbazide in a 0.05 molar glucose buffer adjusted to pH 8.8 with sodium hydroxide, and then impregnating that binder with a 0.4 molar solution of ceric sulfate. Upon exposure to lactic acid, a similarly bright yellow color develops with these reagents.

In each of these methods, the observed color and intensity are dependent upon the amount of lactic acid present. Lactic acid concentrations are preferably standardized through exposure of similarly treated impregnated binders to samples containing known amounts of lactic acid. These various intensities are then presented in a chart or other visual manner so that a person utilizing this method can quickly compare the intensity of color which develops upon testing to the intensity given in a standardized color chart. It should be understood that the indicators described above directly respond to the amount of lactic acid to which they are exposed, and therefore, the volume of vaginal secretions to which they are exposed should be reasonably constant. In the case of a feminine tampon or strip of filter paper, the amount of vaginal secretion to be tested would be expected to be reasonably constant. An alternate embodiment of the present invention would contemplate sampling a predetermined amount of vaginal secretion through an alternate technique and exposing that vaginal secretion directly to a reagent solution, gas chromatograph, or other indicator means which would respond qualitatively and quantitatively to the amount of lactic acid present in a given sample, thereby establishing the concentration of that lactic acid. Since there are extremely dramatic variations in the amount of individual volatile organic compounds present throughout the course of a menstrual cycle, any given technique for measuring the amount of that compound present, used at spaced apart intervals throughout the cycle, will correspondingly produce an indication of the concentration of that organic compound present in the vaginal secretions at the time of sampling. Thus, it can be seen that the specific preferred embodiments discussed above may be adapted to respond qualitatively and quantitatively to the concentration of lactic acid, acetic acid, or other volatile organic compound, depending upon the reagent mixture which is used to impregnate the filter paper, tampon, or other binder.

In the case of urea, the indicator means may be produced as follows: One end of a strip of analytical grade filter paper is dipped into a buffered urease to impregnate it withthat substance. This buffered urease solution generally comprises 150 mg urease and 1.0 g ethylenediaminetetracetic acid per 100 ml water, adjusted to pH of 6.5. The middle of the strip is impregnated with $K_2CO_3$ solution while the top is impregnated with Bromcresol green in tartartic acid. Vaginal secretions are collected for example on a glass rod, and are placed in the bottom of a test tube to which 0.1 ml of water is added. The strip of paper is added, dipping the urease end into the secretion. Free ammonia is developed from the action of urease on the urea. As urea is formed, it migrates up the strip to the $K_2CO_3$, where free $NH_3$ is released. Free ammonia hitting the Bromcresol green turns it from a yellow to a blue-green color. In accordance with the preferred embodiment of the present invention, the strip of analytical grade filter paper is delineated by markings which allows ready comparison between samples. The height the color change reaches up the Bromcresol green portion is then directly readable as a proportion of the volume of $NH_3$ release. Each millimeter of height of color change is equal to 0.05 milligrams of urea per gram of secretion. Levels less than 0.1 milligram urea per gram secretion should produce no color change at all. In this case, the paper strip should be calibrated in 1 millimeter increments at the indicator end.

Alternatively, a second method may be employed using buffered urease solution, phenol color reagent, and alkalihypochlorite reagent. The phenol color reagent comprises 50.0 grams A.R. grade phenol and 0.25 grams A.R. grade sodium nitroprusside per liter, while the alkali-hypochlorite reagent comprises 25.0 grams A.R. grade NaOH and 2.1 grams sodium hypochlorite per liter. The buffered urease solution used in this method is the same as that used above. After collection, the vaginal secretion should be added to 0.2 milliliters of the buffered urease solution. This should be allowed to stand for 30 minutes. Then, 1.0 milliliters of phenol color reagent should be added to each test tube, the solution should be mixed and then 1.0 milliliters of alkali-hypochlorite reagent should be added, and the solution mixed again. It should be noted that the phenol reagent must be added first. The final solution should be allowed to stand for an additional 40 minutes during which time a yellow color will develop which is proportional to the amount of urea present. In order to accurately calibrate the concentration of the amount of urea present in the vaginal secretions, it would be anticipated that for home use a woman would be provided with a kit which would clearly and easily present the steps of the method to be used together with charts and/or standardized vials for color comparison, etc. Methods for the determination of urea have been discussed in Chapter 12 of Clinical Chemistry Principles and Techniques, by Richard J. Henry, M.D., published by the Hoeber Medical Division of Harper and Rowe publishers (1964).

In utilizing the present invention either to diagnose ovulation or to predict the fertile period, a woman would be provided with a kit having indicator means for qualitatively and quantitatively responding to at least one of the volatile organic compounds commonly found in vaginal secretions or urea. She would then use the indicator means provided for monitoring her vaginal secretions, preferably at spaced apart intervals throughout her menstrual period beginning after the cessation of menses. If the fertile period is to be predicted, these intervals should occur at least every 36 hours and preferably every twelve to twenty-four hours until ovulation has passed. In the case of lactic acid, a first lactic acid increase would be observed by this method approximately twelve to twenty-four hours prior to the beginning of the preovulatory estrogen rise, and the woman would be given advance notice that the fertile period would soon begin. A similar method would be used in the case of urea, with the corresponding time period adjustments being made. If intended as a birth control method, she would then abstain from exposure to conception until after observing a second increase in lactic acid concentration occurring at least 4 days after the first lactic acid increase. This second increase, which should correspond to, or in some cases follow ovulation, may be confirmed as the ovulatory increase by using other ovulation indicators such as the acetic acid preferred embodiment of the present invention. It would then be recommended to abstain from exposure to conception for an additional twenty-four to thirty-six hours to insure that the ovum would no longer be fertilizable. A similar technique would be applicable for the woman desiring to conceive, with the exception that she should maximize her exposure to conception during this fertile period. A similar method would be used for diagnosing the occurrence of ovulation, however, of course, alternative indicator means would be employed for responding qualitatively and quantitatively to any desired volatile organic compound commonly found in the vaginal secretions and having a molecular weight of between 50 and 350 grams per mole. Therefore, it can be seen that the indicator means of the present invention provides a reliable "home-test" method by which a female may accurately diagnose the occurrence of ovulation, or alternatively predict the onset and termination of her fertile period.

Figure 7:
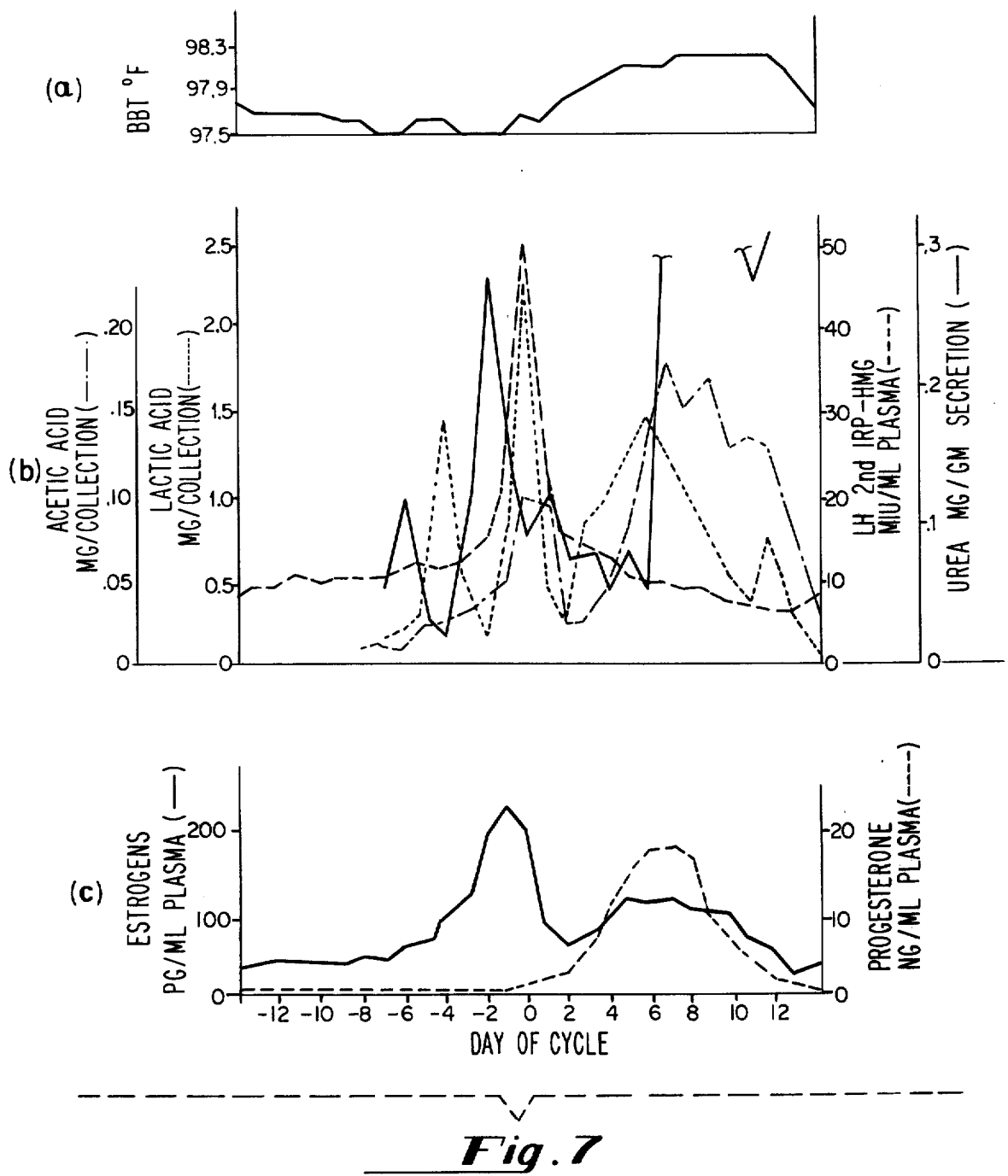
FIG. 7 is a graph of the expected data for basal body temperature lutenizing hormone, progesterone, estrogens, lactic acid, acetic acid and urea over the course of one menstrual cycle.

Referring now to FIG. 7, it can be seen that the cyclic levels of urea, acetic acid, lactic acid, and lutenizing hormone in FIG. 7(b) have been plotted in correlation to basal body temperature which is shown in FIG. 7(a) and the circulating levels of estrogens and progesterone in FIG. 7(c). One of the primary objects of the present invention is to provide a simple, inexpensive home-test means whereby a woman can determine the precise timing not only of the onset of the fertile period and/or of ovulation, but also may determine in advance, with some degree of accuracy, the expected time of each of those occurrences and of menstruation. Referring now to FIG. 7(b), it can be seen that beginning on approximately day −6 (with day 0 being taken as the day of ovulation), a positive indication may be obtained using a simple home-test method which accurately predicts the current stage of the menstrual cycle. In particular, by using a combination of methods to detect urea, acetic acid and lactic acid, it is now possible to receive some type of positive indication on approximately days −6, −4, −2 and 0 of a cycle, and similarly, receive some reasonable indication of the occurrence of the luteal phase of the menstrual cycle. While in most cases, it is not expected that elaborate plotting techniques will be employed by the average woman solely for the purpose of determining the fertile period, the methods of the present invention will, nonetheless, prove extremely valuable to medical practitioners such as obstetricians, gynecologists, and possibly endocrinologist who are interested in using secondary characteristics to diagnose diseases or other abnormalities which affect sex steroid variations during the course of the menstrual cycle. For these practitioners the gas chromatographic detection means may be the method of choice for following the cyclical changes in the organic compounds described herein.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. A method of diagnosing the onset of the fertile period or ovulation in female mammals comprising the steps of:
   a. monitoring the variation in concentration of the vaginal secretions of one of said mammals for urea, said variation corresponding to the onset of the fertile period or ovulation of said mammal; and
   b. providing an indicator means for qualitatively and quantitatively responding to the concentration of said urea in said vaginal secretions; whereby the response of said means is diagnostic of the onset of the fertile period or ovulation in said female mammal.

2. The method of claim 1, wherein said indicator means comprises at least one chemically inert binder impregnated with chemical means for detecting the concentration of said urea.

3. The invention of claim 2, wherein the concentration of the urea is monitored by bringing each of a plurality of said binders into contact with the vaginal secretions of said female mammal at spaced apart intervals to determine variations in concentration of said organic compound in said secretions.

4. A method of diagnosing the onset of the fertile period or ovulation in a given female mammal comprising the steps of:
   a. monitoring the variation in concentration of the vaginal secretions of said mammal for at least urea, said variation corresponding to the onset of the fertile period or ovulation of said mammal, by
   b. providing indicator means for qualitatively and quantitatively responding to the concentration of said urea in said vaginal secretions; and
   c. evaluatisng the correspondence of the variation in concentration of said urea to the time of ovulation as indicated by other ovulation indicators; whereby said evaluation is diagnostic of ovulation in said given mammal.

5. The invention of claim 4, wherein said indicator means comprises at least one chemically inert binder impregnated with chemical means for detecting the concentration of said urea.

6. The invention of claim 5, wherein the concentration of the urea is monitored by bringing each of a plurality of said binders into contact with the vaginal secretions of said female mammal at spaced apart intervals to determine variations in concentration of said urea in said secretions.

7. A method of predicting the fertile period of female mammals comprising the steps of:
   a. monitoring the variation in concentration of the vaginal secretions of one of said mammals for at least urea by beginning said monitoring at the cessation of the menses, said variation corresponding to the onset of the fertile period or ovulation of said mammal; and
   b. providing an indicator means for qualitatively and quantitatively responding to the concentration of said compound in said vaginal secretions; whereby the response of said means predicts the onset of the fertile period or ovulation of said mammal.

8. The invention of claim 7, wherein a first response of said indicator means indicating an increase in said urea concentration predicts the onset of the fertile period of said female mammal by at least 2 days.

9. The invention of claim 8, wherein a second response of said indicator means indicating an increase in said urea concentration and occurring at least four days after said first response predicts ovulation by at least 2 days.

10. The invention of claim 9, wherein said indicator means comprises at least one chemically inert binder impregnated with chemical means for detecting the concentration of said urea.

11. The invention of claim 10, wherein the concentration of urea is monitored by bringing each of a plurality of said binders into contact with the vaginal secretions of said human female at spaced apart intervals to determine the occurrence of said first and second responses.

12. The invention of claim 11, wherein said indicator means also qualitatively and quantitatively responds to the concentration of a volatile organic acid selected from the group consisting of acetic acid and lactic acid in said vaginal secretions, and wherein a first response indicating an increase in said organic acid and occurring at least 6 days after said first urea response is indicative of ovulation.

13. A method of predicting the fertile period of a given female mammal comprising the steps of:
   a. monitoring the variation in concentration of the vaginal secretions of said female mammal for at least the urea found in said vaginal secretions, beginning after the cessation of menses, said variation corresponding to onset of the fertile period of said mammal, by
   b. providing indicator means for qualitatively and quantitatively responding to said concentration of urea; and
   c. evaluating the correspondence of said variation in concentration to the fertile period as indicated by other ovulation indicators; whereby said evaluation is diagnostic of ovulation for said given mammal.

14. The invention of claim 13, wherein said indicator means is a gas-chromatograph.

15. The invention of claim 14, wherein said indicator means is brought into contact with the vaginal secretions of said female mammal at spaced apart intervals to determine variations in concentration of said urea.

16. The invention of claim 15, wherein said spaced apart intervals occur at least every thirty-six hours.

17. A method of predicting the fertile period of a human female comprising the steps of:
   a. impregnating a plurality of binders with chemical means for detecting the concentration of urea thereby forming a plurality of impregnated binders;
   b. bringing each of said impregnated binders into contact with the vaginal secretions of said female at spaced apart intervals to determine the variations in concentration of urea present in said secretions; and
   c. observing the variations in concentration of urea in said secretions as indicated by said impregnated binder, a normal concentration of said urea appearing after the cessation of menses; a first increase in said urea concentration over said normal concentration predicting the onset of said fertile period by at least 2 days, and a second increase over said normal concentrations occurring at least 4 days after said first increase predicting ovulation by at least 2 days.

18. The invention of claim 17, wherein said binders are feminine tampons.

19. The invention of claim 17, wherein said chemical means for detecting the concentration of urea respond with a color change reaction which gives a direct linear indication on said means of the concentration of said urea.

20. A birth control method comprising the steps of:
   a. predicting the fertile period of a female mammal by monitoring the variation in concentration of the vaginal secretions of said mammal for urea by beginning said monitoring at the cessation of menses;
   b. providing an indicator means for qualitatively and quantitatively responding to the concentration of said urea in said vaginal secretions whereby a first response of said indicator means indicating an increase in said urea concentration predicts the onset of the fertile period of said female mammal by at least two days, and wherein a second response of said indicator means indicating an increase in said urea concentration and occurring at least four days after said first response predicts ovulation by at least two days, and c. causing said mammal to avoid exposure to fertilization beginning no more than two days after said first increase and ending at least seventy-two hours after said second increase.

* * * * *